United States Patent [19]

Fabian

[11] Patent Number: 5,077,778
[45] Date of Patent: Dec. 31, 1991

[54] FILM CASSETTE HAVING MARKER FOR IDENTIFYING THE EXPOSURE SIDE OF A MEDICAL RADIOGRAPH

[76] Inventor: Carl E. Fabian, 577 N.E. 96th Street, Miami Shores, Fla. 33138

[21] Appl. No.: 572,392

[22] Filed: Aug. 27, 1990

[51] Int. Cl.$^5$ .................................................. H05G 1/28
[52] U.S. Cl. ................................... 378/162; 378/165; 378/166
[58] Field of Search ............... 378/162, 165, 182, 184, 378/166, 187

[56] References Cited

U.S. PATENT DOCUMENTS

| | | | |
|---|---|---|---|
| 2,426,286 | 8/1947 | Stadler | 378/165 |
| 3,628,864 | 12/1971 | Fessenden et al. | 378/166 |
| 3,668,394 | 6/1972 | Panzer | 378/165 |
| 3,703,272 | 11/1972 | Lareau | 378/166 |
| 4,383,329 | 5/1983 | Kröbel et al. | 378/166 |
| 4,429,412 | 1/1984 | Pierce et al. | 378/165 |
| 4,510,392 | 4/1985 | Litt et al. | 378/162 |
| 4,520,497 | 5/1985 | Kluge et al | 378/166 |
| 4,698,836 | 10/1987 | Minasian | 378/162 |
| 4,953,193 | 8/1990 | Robinson | 378/162 |
| 4,972,450 | 11/1990 | Carlile et al. | 378/166 |

Primary Examiner—Janice A. Howell
Assistant Examiner—Kim-Kwok Chu
Attorney, Agent, or Firm—Ernest D. Buff

[57] ABSTRACT

The present invention provides an X ray film cassette with a permanent marking means for identifying the side of the radiographic film that faced the X ray tube during exposure. Such identification is achieved irrespective of whether the film is exposed through the cover or base of the cassette and does not require any separate action by the X ray technologist, eliminating the element of human error. In a preferred embodiment, the working means is comprised of chirally asymmetric X ray opaque and/or light-opaque letters or markings permanently mounted in the film cassette. A user friendly apparatus is described, for installing the light-opaque markers on the intensifying screens of the X ray film cassette.

23 Claims, 9 Drawing Sheets

FILM CASSETTE HAVING MARKER FOR IDENTIFYING THE EXPOSURE SIDE OF A MEDICAL RADIOGRAPH

BACKGROUND OF THE INVENTION

1. Field of the Invention

The present invention relates to the field of medical radiography; and more particularly to means for positively identifying the exposure side or front side of an X ray film.

2. Description of the Prior Art

A medical radiograph is the X ray image of some part of the body produced by an X ray beam originating from an X ray tube. The X ray beam passes first through the body and then through an X ray film cassette which is a light-proof, flat box of rigid construction. It is typically comprised of a base with a central recess to receive the film, and a cover joined to the base by hinges and containing latches permitting it to be opened and securely closed when a film is loaded. In order to diminish the X ray dose required to obtain a proper exposure of the film the inside surfaces of the cassette are lined with "intensifying screens" which sandwich the film between them. The X ray beam passing through the intensifying screens causes them to fluoresce and give off visible light which in turn exposes the film from both sides. Since the X ray film is much more sensitive to the visible light than to the X ray beam, most of the film exposure actually results from the induced light. The presence of the screens therefore allows the optimal film exposure to be achieved at significantly lower radiation doses than would otherwise be needed. Once the film is exposed, it is brought to the dark room, removed from the cassette and developed, causing the latent image to become visible. The radiograph is then ready for viewing and interpretation.

Since the film must be identified with pertinent information such as patient's name, date, etc., the cassette is also provided with what is herein called a "blocker". This blocker is generally comprised of two opposing strips of lead mounted on the inside surfaces of the cassette which shield the area of film between them from becoming exposed by either the X ray beam or its induced light. When the technologist is ready to develop the film a card bearing the appropriate patient data is placed into a device which light-flashes the card, thereby projecting the data onto the unexposed area produced by the blocker. The position of the blocking rectangle within the cassette is not constant and may vary with the manufacturer, individual X ray department, and even from one cassette type to another within the same department.

Apparatus and methods, including modifications of the film cassette for marking exposed X ray film or radiographs with patient data are disclosed, for example by U.S. Pat. Nos. 3,628,864, 3,703,272, 4,465,364, 4,510,392, 4,806,959, 4,383,329, 4,520,497, and 4,768,114.

When rendering a diagnosis from a radiograph it is necessary for the film reader to know which side of the body is being viewed. Since the body is generally symmetrical, right-sided structures are similar in appearance to left-sided structures except that they are mirror-images or reversals of one another. For example, an X ray image of a left foot if viewed from the back of the exposed film will look like a right foot. Since radiographs are typically transparent and can be viewed from either side, it is therefore possible for X ray images of one side of the body to become confused with the other. For this reason when a medical radiograph is performed of some part of the body it is customary for the technologist to affix an X ray opaque "R" or "L" marker on the cassette cover adjacent to the part being X-rayed to indicate which side of the body is represented on the film. Not infrequently however, the technologist places the wrong marker on the cassette or for one reason or another the marker is not visible on the film, being either obscured or omitted, so that the technologist is required to mark the film after it is developed, using an adhesive label, wax pencil, ink, or even scratch marks. Further complicating the issue, the technologist may sometimes inadvertently expose the cassette through the base rather than through the cover, which is the customary side to expose. The incidence of incorrect or absent right/left marking due to human error is quite substantial, reportedly as high as 30%. If a film is improperly marked and the physician interpreting the film recognizes the error he will often try to locate the technologist who performed the study to obtain clarification. When the question cannot be resolved in this manner, the patient may be recalled for a repeat examination which involves time, inconvenience, expense and additional radiation exposure. Furthermore, if the error should go undetected, inappropriate medical treatment may be the result.

Since the primary cause of this right/left confusion stems from the fact that the film is transparent and may be viewed from the front (exposure side) or the back, identifying the front side of the film for the viewer will prevent the inadvertent viewing of the film from the wrong side and thereby permit ready determination of which side of the body is represented thereon.

There is no means described in the prior art for permanently modifying the film cassette to expressly indicate the exposure side of the film, positively and regardless of the direction of exposure.

SUMMARY OF THE INVENTION

The present invention provides an X ray film cassette with a permanent marking means for identifying the side o the radiographic film that faced the X ray tube during exposure. Such identification is achieved irrespective of whether the film is exposed through the cover or base of the cassette and does not require any action by the X ray technologist, eliminating the element of human error. In a preferred embodiment, the working means is comprised of chirally asymmetric X ray opaque and/or light-opaque letters or markings permanently mounted in the film cassette.

Generally stated, markers are permanently mounted in the film cassette, providing the cassette with means for marking the X ray film during exposure with an image indicating the direction of exposure and hence the side of the film which faced the X ray tube during exposure.

In one aspect, the invention provides a radiographic film cassette for exposing a sheet of film to X rays projected along an X ray path by an X ray tube. The cassette includes a cover having an inner surface defining a recess for receiving the film sheet. A base having an inner surface is adapted to close upon the cover, securing the film sheet. The cassette has a first intensifying screen immovably disposed within the recess between the film sheet and the inner surface of the cover. A first chirally asymmetric and X ray opaque marker is permanently mounted to the cover to intersect a portion of the X ray path during exposure. A second intensifying screen is immovably disposed between the film sheet and the inner surface of the base. The cassette optionally includes a second chirally asymmetric and X ray opaque marker permanently mounted to the base to intersect a portion of the X ray path during exposure. The film sheet, upon exposure, bears an image of that marker situated between the film sheet and the X ray tube during exposure. The presence on the film sheet of an image of the first marker indicates that the X ray path proceeded from the tube through the cover to the film. On the other hand, the image on the film sheet of the second marker (or the absence of any marker image on the film sheet if only on marker is used and that marker is permanently mounted on the cover) indicates that the X ray path proceeded from the tube through the base to the film.

In another aspect of the invention, the first and second markers are light-opaque. The first marker is permanently fixed to the first intensifying screen and adjacent to the film. The second marker is the mirror image of the first marker when viewed from the inside of the open cassette, and the second marker is permanently fixed to the second intensifying screen and adjacent to the film to intersect the same portion of the X ray path as the first marker. The film sheet, upon exposure, bearing a composite image of both the first and second markers. Optionally, only one screen bears a light-opaque marker.

An apparatus is described for installing a plurality of light-opaque markers on active sides of a plurality of intensifying screens disposed in an X ray film cassette, comprising: first and second markers, each being light opaque and chirally asymmetric; first and second applique sheets carrying the first and second markers, respectively, each of the applique sheets having an adhesive surface in contact with an anti stick protective sheet, adapted for removal to unmask adhesive thereon; and spacing means comprising a spacer sheet having first and second planar surfaces provided with adhesive adapted for temporary contact with the first and second applique sheets, respectively, to thereby form a marker installation assembly; whereby disposition of the marker installation assembly on an active side of one of the intensifying screens with the adhesive surfaces unmasked is operative, upon closing the cassette, to adhesively secure the applique sheets to the intensifying screens in an aligned condition.

Optionally, the cassette comprising the first and second light opaque markers further comprises a third marker permanently fixed to the inner or outer surface of the base or between the base and the second intensifying screen. The third marker being X ray opaque and situated to encompass a portion of the X ray path. In addition, an X ray opaque obscurant is permanently fixed to the inner or outer surface of the base or between the base and the second intensifying screen or combined with the third marker The obscurant being situated to encompass at least the same portion of the X ray path intersected by the first and second markers, whereby the film sheet, upon exposure to X rays emitted from the X ray tube located on the base side of the cassette, bears an image of the third marker and the obscurant, the obscurant blocking exposure of image of the first and second markers.

In use, the invention provides information concerning identification of the X ray path leading to exposure of the film sheet, which positively identifies the exposure side or front of the film. The information is provided by means which are user friendly and virtually eliminate the element of human error. Positive identification of the side of the film sheet facing the X ray tube during exposure permits more accurate diagnosis and results in fewer repeat examinations, thereby reducing the attendant inconvenience, expense and total radiation exposure to the population at large and improving the quality of medical care. Additionally, the information is copied to reproductions of the film.

BRIEF DESCRIPTION OF THE DRAWINGS

The invention will be more fully understood and further advantages will become apparent when reference is made to the following detailed description of the preferred embodiment of the invention and the accompanying drawings, in which.

DESCRIPTION OF THE PREFERRED EMBODIMENTS

Figure 1:
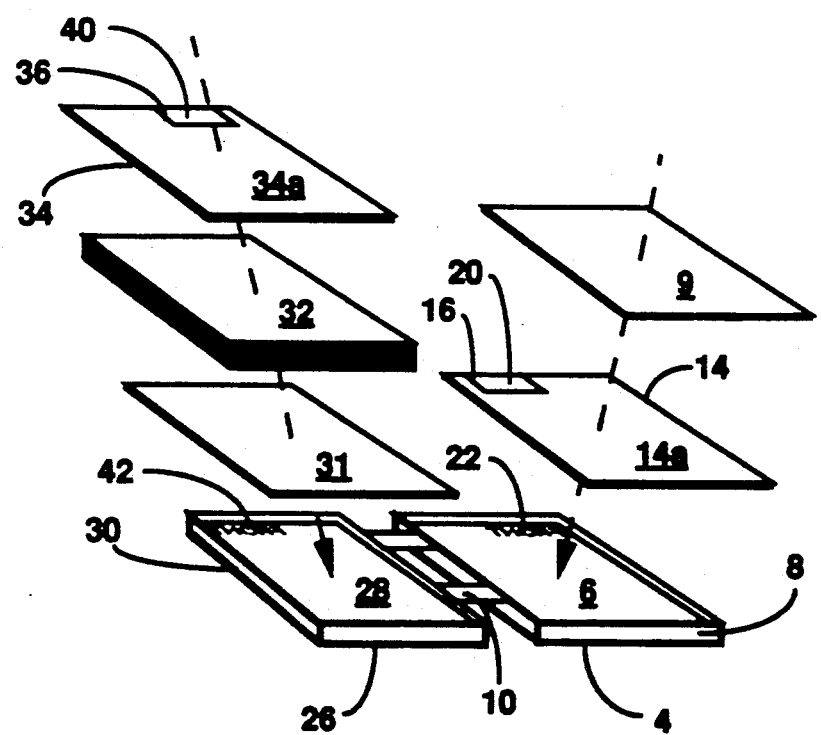
FIG. 1 is an exploded view of an X ray film cassette.

Referring to FIG. 1 of the drawings, there is shown an X ray film cassette 2 having molded cover 4 of aluminum, plastic, or other suitable material which is transparent to X rays and which is of rigid construction. Cover 4 has a flat inner surface 6 and upstanding flanges 8 encompassing the periphery of surface 6 to provide a recess for receiving a sheet of film 9. One or more hinges 10 are mounted along one of the flanges for attaching a base 26. A first intensifying screen 14 having an active surface 14a comprising a fluorescent material is attached to the inner surface 6. The first intensifying screen 14 is provided with a rectangular cutout 16 along one edge to receive X ray opaque blocking rectangle 20. Typically, blocking rectangle 20 comprises lead sheet of approximately 1 inch by 3 inches. Markers 22 and 42 comprise lead sheet or other X ray opaque material in the shape of a symbol, word or letter that is chirally asymmetric. Chiral asymmetry provides a marker with a mirror image that is different from itself. Preferably, markers 22 and 42 comprise a symbol that expressly indicates the front or exposure side of the film, such as "F", "FRONT", VIEWING SIDE, TUBE SIDE, EXPOSURE SIDE, etc., since film 9 is normally viewed from the exposure side. Letters such as B, C, D, etc., and almost any word or sequence of words or letters in which the mirror image is different are chirally asymmetric and can be utilized. On the other hand, isolated letters such as "A", "O", "I""T" and words such as "XIX", by virtue of their chiral symmetry would not be suitable. Typically, marker 22 is situated to the side of blocking rectangle 20. Further the marker 22 is fixed between intensifying screen 14 and cover 4, or marker 22 is fixed to the outside of cover 4, or marker 22 is fixed to inner surface 6 of cover 4. Marker 22 is oriented to read correctly when viewed through cover 4 from the outside of cassette 2. X rays entering cassette 2 through cover 4 are blocked from exposing the section of film 9 under marker 22 and blocking rectangle 20, thereby imparting an image of marker 22 and blocking rectangle 20. The unexposed portion of film 9 under blocking rectangle 20 can later be exposed with patient data by the technologist.

Again referring to FIG. 1, a molded base 26 is formed of aluminum, plastic or other suitable material which is transparent to X rays and which is of rigid construction. Base 26 has a flat inner surface 28 and upstanding flanges 30 encompassing the periphery of surface 28 to provide a recess for receiving cover 4. Flange 30 is connected along one side to hinges 10. A foam pad 32 attached to the inner surface 28 of base 26 carries a second intensifying screen 34 having an active surface 34a comprising a fluorescent material. The second intensifying screen 34 having a cutout 36 provided to receive a second blocking rectangle 40. Typically, blocking rectangle 40 comprises lead sheet of approximately 1 inch by 3 inches. A sheet of lead 31 may be interposed between pad 32 and inner surface 28. Typically, cutout 36 and blocking rectangle 40 are identical to their respective counterparts 16 and 20 in cover 4 and are arranged so that the blocking rectangles 20 and 40 are stacked one over the other when the cassette 2 is closed. Marker 42 is situated to the side of blocking rectangle 40. Further the marker 42 is fixed between intensifying screen 34 and base 26, or marker 42 is fixed to inner surface 28 of base 26, or marker 42 is fixed to the outside of base 26. Marker 42 is oriented on base 26 to read correctly when viewed through base 26 from the outside of cassette 2. X rays entering the cassette 2 through base 26 are blocked from exposing the section of film 9 under marker 42 and blocking rectangle 40, thereby imparting an image of marker 42 and blocking rectangle 40. The unexposed portion of film 9 under blocking rectangle 40 can later be exposed with patient data by the technologist.

Placement of markers 22 and 42 on the outside of cover 4 and base 26, respectively, is particularly useful when retrofitting existing cassettes.

Figure 2A:
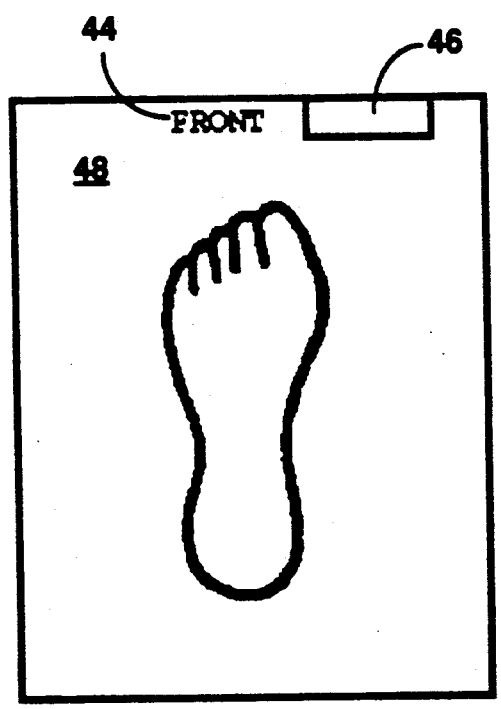
FIGS. 2a and 2b are an exposure side view of an X ray film and a view from the back of an X ray film, respectively.
Figure 2B:
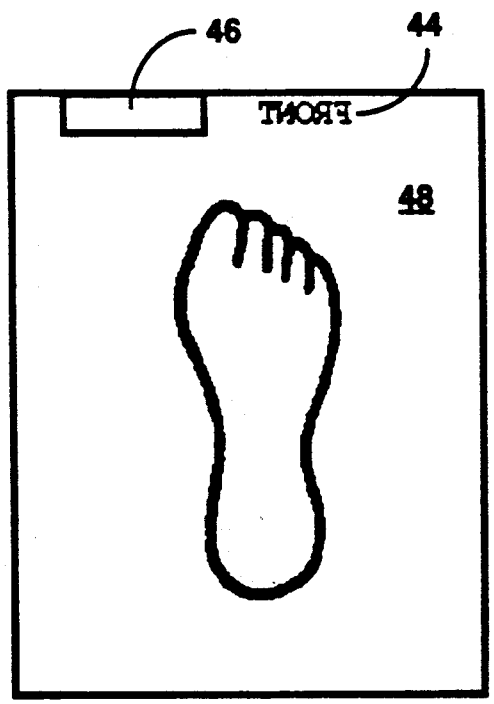

A radiograph of a left foot exposed in the usual way, through the cover of the cassette, is shown in FIGS. 2a and 2b. When viewed from the front or exposure side of film 48, as shown in FIG. 2a, marker image 44 is readable and the anatomy of the foot is also displayed in the correct orientation. Conversely, when film 48 is viewed from the back side, as shown in FIG. 2b, the orientation of the anatomy is reversed making it appear like a right foot, but the marker image 44 is also reversed warning that the view is from the back side of film 48. Blocking rectangle image 46 is also shown in the figures.

Figure 3:
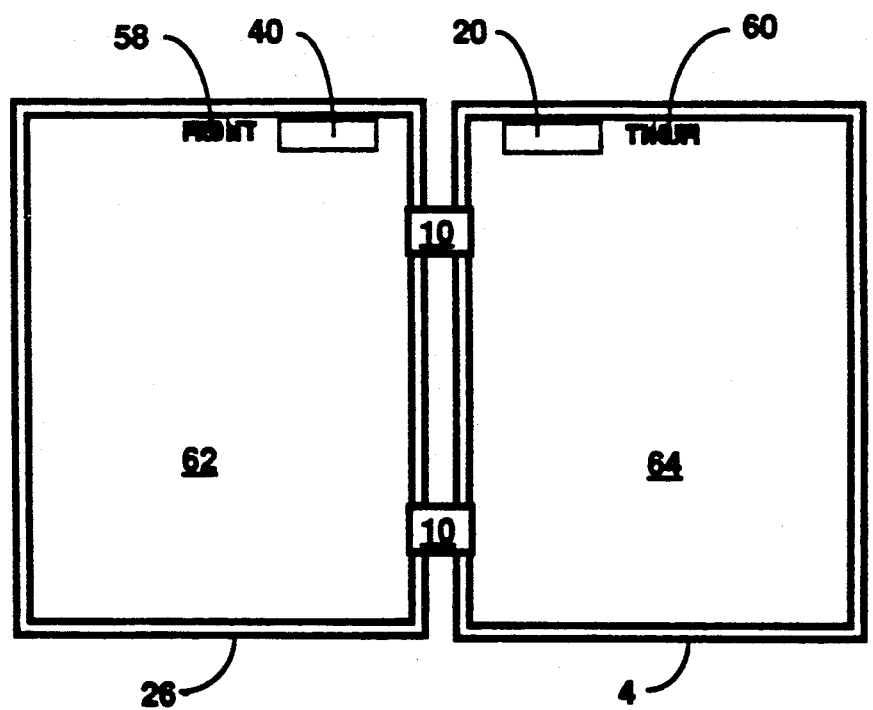
FIG. 3 is a view of the inside of an open cassette equipped with stand-alone light-opaque markers.

Shown in FIG. 3 is an embodiment useful when retrofitting existing cassettes, particularly under circumstances wherein orientation of cassette 2 during exposure is not a variable. Cassette 2 is constructed as above but instead, the chirally asymmetric markers are comprised of light-opaque material, such as black ink, paint, printed decal or similar marking, or X ray opaque lead foil. Cutting away or removing a portion of the intensifying screen in the desired shape would have the same effect. The markers 58 and 60 are located on the inner surfaces of intensifying screens 62 and 64, and generally along the edge thereof. Markers 58 and 60 are oriented such that they line up exactly one over the other when cassette 2 is closed, and are read properly if viewed through cover 4. That is, with the cassette open, marker 58 is in its readable orientation, and marker 60 is read as the mirror image of marker 58.

Figure 4:
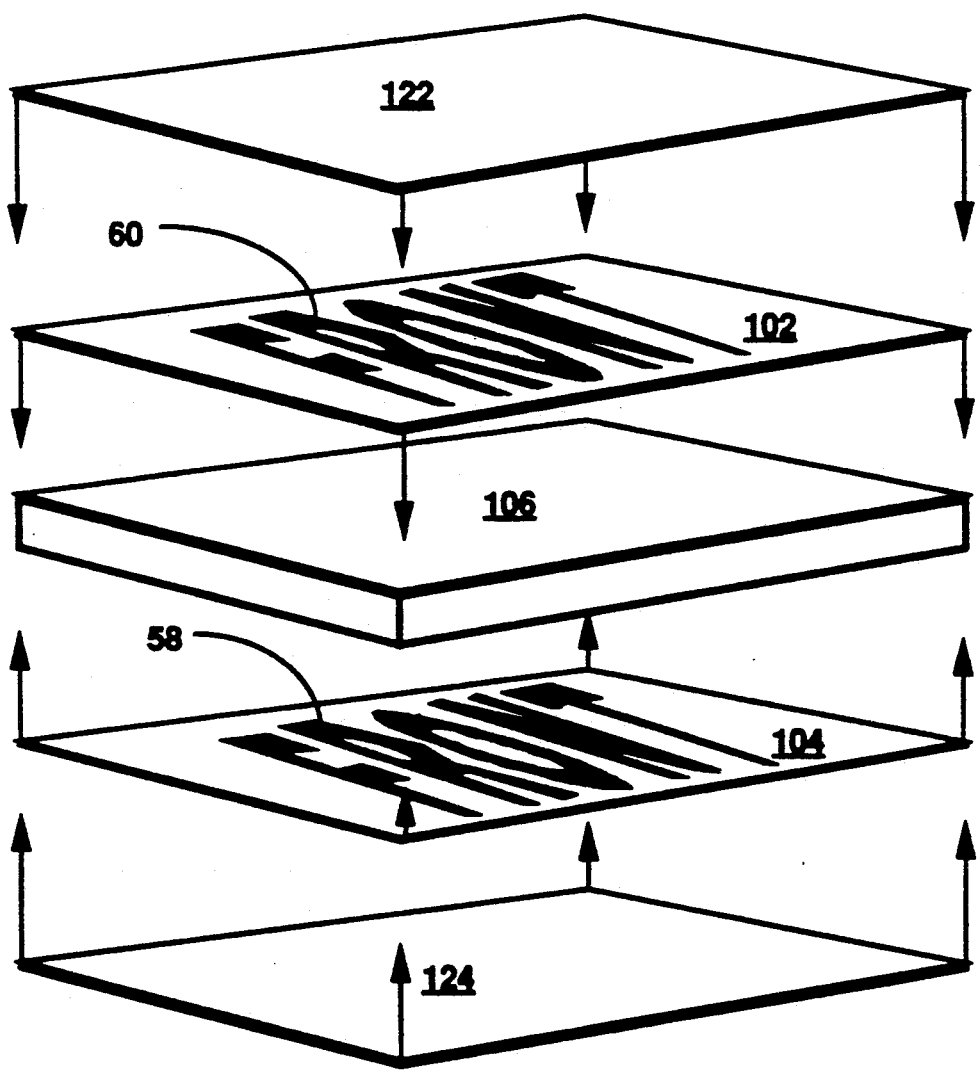
FIG. 4 is an exploded view of the apparatus to install light opaque markers on the intensifying screens.
Figure 5:
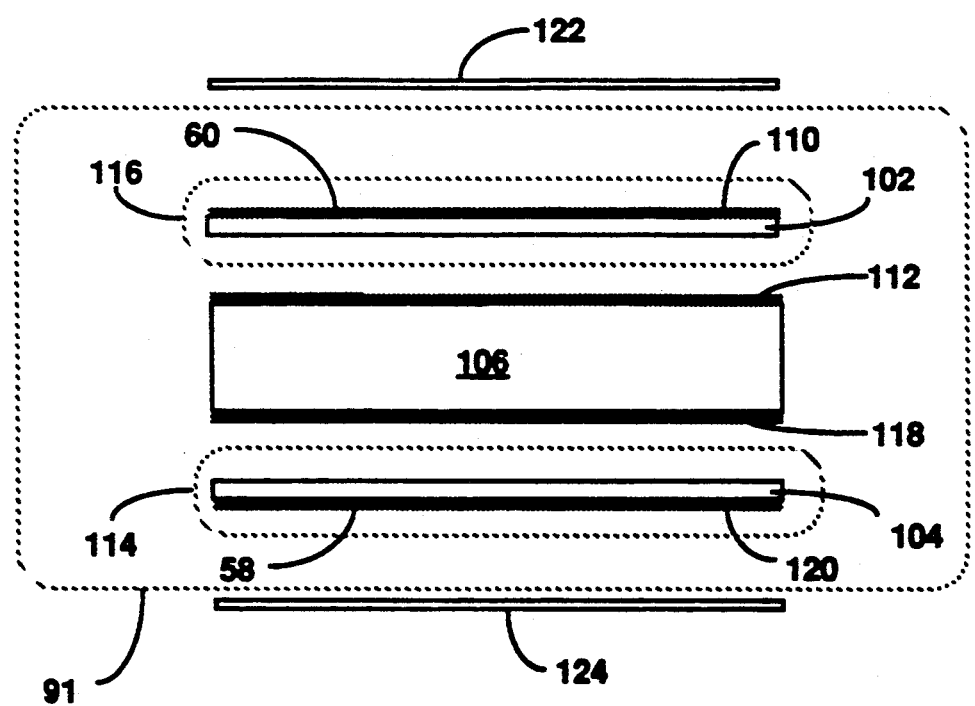
FIG. 5 is a side view of apparatus to install light-opaque markers on the intensifying screens.

Shown in FIGS. 4 and 5 is an apparatus 90 to facilitate installation of light-opaque markers 58 and 60 in cassette 2, the apparatus being about ⅛ inch in thickness. Apparatus 90 comprises a marker installation assembly 91 and anti-stick protective sheets 122 and 124. Applique 116 comprises light-transparent or translucent sheet 102, light opaque marker 60, and permanent, adhesive coating 110, such as a pressure sensitive adhesive. Similarly, applique 114 comprises light-transparent or translucent sheet 104, light-opaque marker 58, and permanent, adhesive coating 120. Preferably, the adhesive coatings 110 and 120 exhibit clarity and resistance to ultraviolet and X ray aging, such as but not limited to, polyvinyl ethel ether, polyisobutylene, or acrylate copolymer based coatings. The sheets 102 and 104 are composed of cellophane, polyvinyl chloride, polyester, polyethelene, polypropylene, cellulose acetate or similar films. The adhesive coatings 110 and 120 are temporarily protected by the anti-stick protective sheets 122 and 124 respectively. The protective sheets 122 and 124 are comprised of paper or similar web material having anti-stick coatings, such as cured dimethyl silicone or wax. These anti-stick protective sheets 122 and 124 have significantly lower surface energy than the surface tension of the adhesive coatings 110 and 120, and will therefore separate easily from the adhesive coatings. Typically the surface energy of the anti-stick protective sheets 122 and 124 is less than about 80%, preferably less than about 50%, more preferably ranges up to 25% of the surface tension of the adhesive coatings. Spacer 106 is comprised of a disposable material such as paper, cardboard, or foam pad, and the spacer has both faces covered with adhesive coatings 112 and 118. The adhesive coatings 112 and 118 have surface tensions significantly greater than the surface energies of appliques 114 and 116 respectively, and are thereby adapted to temporarily hold the appliques. Typically the surface tension of the adhesive coatings 112 and 118 is greater than about 125%, preferably greater than about 200%, more preferably ranges above 400% of the surface energy of the appliques 114 and 116. To use apparatus 90, protective sheets 122 and 124 are stripped from marker installation assembly 91 and the exposed adhesive surface 120 is pressed against and along the periphery of the active surface 34a of the screen 34 disposed in open cassette 2, until firmly secured. Fully closing and reopening cassette 2 causes applique 116 to permanently affix to the active surface 14a of the screen 14, and the spacer 106 to separate at one of its adhesive surfaces 112 or 118, permitting removal and disposal of the spacer 106. Whereby, appliques 114 and 116 are permanently transferred to their respective intensifying screens 34 and 14, and markers 58 and 60 are then lined up exactly one over the other. Although the above described apparatus is the preferable way to install markers on intensifying screens, optionally a single light-opaque marker having an adhesive surface is manually attached to either intensifying screen.

Figure 6:
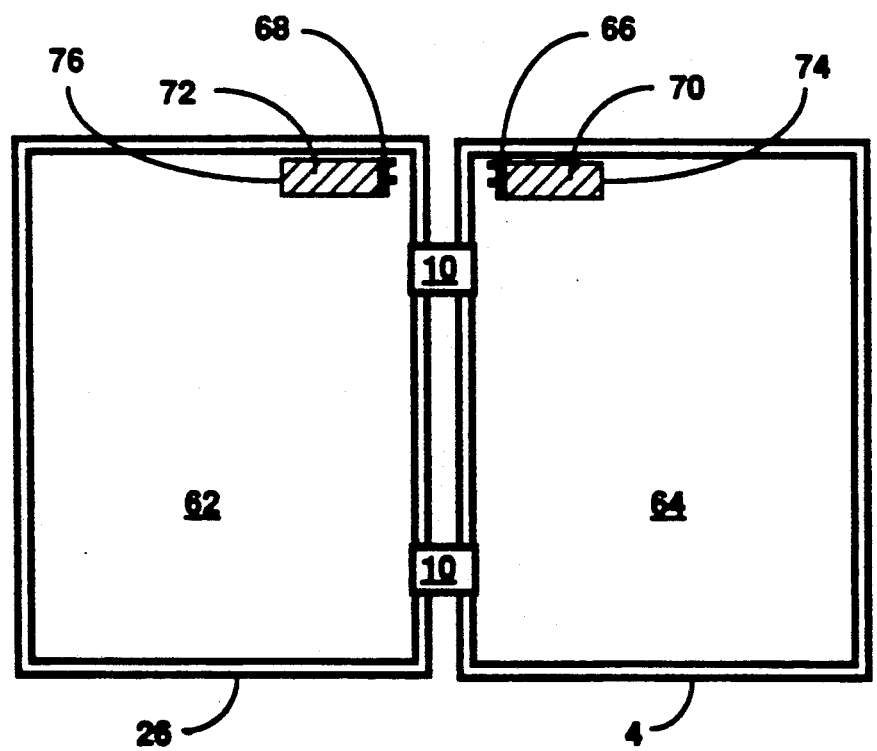
FIG. 6 is a view of the inside of an open cassette equipped with combined marker/blocking-rectangles.

Alternatively, as shown in FIG. 6 markers 66 and 68 can be integrated with the blocking rectangles 70 and 72, respectively, as a contiguous extension of the blocking rectangles, with the shape of blocker cutouts 74 and 76 being adapted to receive the extended rectangles.

Figure 7A:
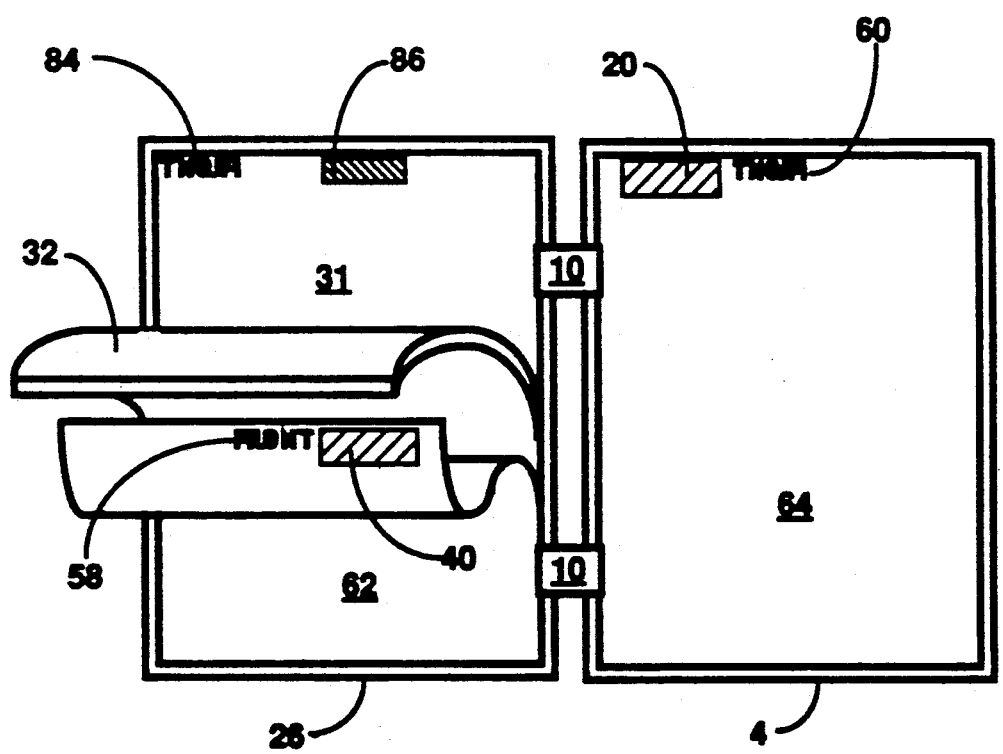
FIGS. 7a and 7b are views of the inside of an open cassette with light-opaque and X ray opaque markers separated from their associated blocking rectangles and obscurants, and light-opaque and X ray opaque markers combined with their associated blocking rectangles and obscurants, respectively.

Still another embodiment employs light-opaque markers on the intensifying screens combined with an X ray opaque marker Referring to FIG. 7a, light-opaque markers 58 and 60 are placed on their respective intensifying screens 62 and 64 as in the preceding embodiment. X ray opaque obscurant 86 and chirally asymmetric X ray opaque marker 84 are situated behind base intensifying screen 62, or on the inside or outside surfaces of base 26. The size, shape, and position of the obscurant 86 being to overshadow and block exposure of the light-opaque markers 58 and 60 when X-rayed through the base of the film cassette. Upon exposure through cassette base 26, film bears image of the X ray opaque marker 84 and the X ray opaque obscurant 86 and composite image of blocking rectangles 20 and 40. Upon exposure through cassette cover 4, film bears composite image of the light-opaque markers 58 and 60 and composite image of blocking rectangles 20 and 40.

Figure 7B:
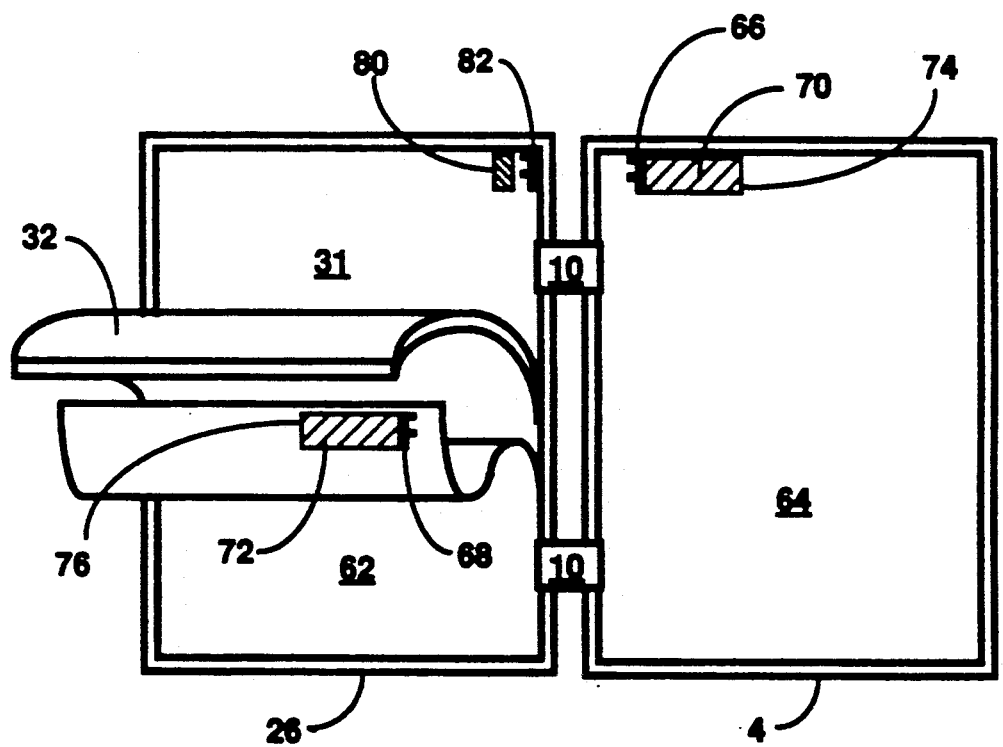

As shown in FIG. 7b, the light-opaque markers 66 and 68 can be combined with blocking rectangles 70 and 72 respectively, and X ray opaque marker 82 can be combined with obscurant 80 which is situated to overshadow markers 66 and 68. Upon exposure through cassette base 26, film bears image of the X ray opaque marker 82 and the X ray opaque obscurant 80 and composite image of blocking rectangles 20 and 40. Upon exposure through cassette cover 4, film bears composite image of the light-opaque markers 58 and 60 and composite image of blocking rectangles 20 and 40.

The markers described above may be variously disposed along every margin of the cassette, within the corners, or along the entire periphery of the cassette.

The invention has been described in detail with particular reference to the preferred embodiments thereof, but it will be understood that additional variations and modifications may suggest themselves to one skilled in the art, all falling within the scope of the invention as defined by the subjoined claims.

What is claimed is:

1. A radiographic film cassette for exposing a sheet of film to X rays projected along an X ray path by an X ray tube, comprising:
   (a) a cover having an inner surface defining a recess for receiving said film sheet;
   (b) a base having an inner surface adapted to close upon said cover for securing said film sheet;
   (c) a first intensifying screen immovably disposed within said recess between said film sheet and the inner surface of said cover;
   (d) a first marker, permanently mounted to said cover to intersect a portion of said X ray path during exposure;
   (e) a second intensifying screen immovably disposed between said film sheet and the inner surface of said base;
   (f) a second marker permanently mounted to said base to intersect a portion of said X ray path during exposure;
   said film sheet, upon exposure, bearing an image of that marker situated between the film sheet and the X ray tube during exposure.

2. A film cassette as recited in claim 1, wherein said first and second markers are X ray opaque.

3. A film cassette as recited in claim 2, wherein said first marker is mounted on the outside of said cover.

4. A film cassette as recited in claim 2, wherein said second marker is mounted on the outside of said base.

5. A film cassette as recited in claim 2, wherein said cassette further comprises a first and second blocking rectangle located, respectively, along an edge of said first and said second intensifying screens to intersect a portion of said X ray path.

6. A film cassette as recited in claim 2, wherein said cassette further comprises a foam pad attached to the inner surface of said base and carries said second intensifying screen.

7. A film cassette as recited in claim 2, wherein said cassette further comprises a sheet of lead interposed between said foam pad and inner surface of said base.

8. A radiographic film cassette for exposing a sheet of film to X rays projected along an X ray path by an X ray tube, comprising:
   (a) a cover having an inner surface defining a recess for receiving said film sheet;
   (b) a base having an inner surface adapted to close upon said cover for securing said film sheet;
   (c) a first intensifying screen immovably disposed within said recess between said film sheet and the inner surface of said cover;
   (d) a first marker, permanently fixed to said first intensifying screen and adjacent to said film to intersect a portion of said X ray path during exposure, said marker being light-opaque;
   (e) a second intensifying screen immovably disposed between said film sheet and the inner surface of said base;
   (f) a second marker, permanently fixed to said second intensifying screen and adjacent to said film to intersect a portion of said X ray path during exposure, said marker being light-opaque;
   said film sheet, upon exposure, bearing an image of each of said markers.

9. A film cassette as recited in claim 8, wherein said second marker is the mirror image of said first marker, said mirror image being situated within the same portion of said X ray path intersected by said first marker.

10. A film cassette as recited in claim 8, wherein said cassette further comprises a third marker permanently fixed to the inner or outer surface of said base or between said base and said second intensifying screen, said third marker being situated to encompass a portion of said X ray path, whereby said film sheet, upon exposure to X rays emitted from said X ray tube located on base side of said cassette, bears an image of said third marker.

11. A film cassette as recited in claim 10 wherein said cassette further comprises an X ray opaque obscurant permanently fixed to the inner or outer surface of said base or between said base and said second intensifying screen or combined with said third marker, said obscurant being situated to encompass the same portion of said X ray path intersected by said first and second markers, whereby said film sheet, upon exposure to X rays emitted from said X ray tube located on base side of said cassette, bears an image of said third marker and said obscurant, said obscurant blocking exposure of image of said first and second markers.

12. A film cassette as recited in claim 8, wherein said first and second markers are cutouts in the first and second intensifying screens respectively.

13. An apparatus for installing a plurality of light-opaque markers on active sides of a plurality of intensifying screens disposed in an X ray film cassette, comprising:
   (a) first and second markers, each being light-opaque and chirally asymmetric;
   (b) first and second applique sheets carrying said first and second markers, respectively, each of said sheets having an adhesive surface in contact with an anti-stick protective sheet, adapted for removal to unmask adhesive thereon; and
   (c) spacing means comprising a spacer sheet having first and second planar surfaces provided with adhesive coating adapted for temporary contact with said first and second applique sheets, respectively, to thereby form a marker installation assembly;
   whereby disposition of said marker installation assembly on an active side of one of said intensifying screens with said adhesive surfaces unmasked is operative, upon closing said cassette, to adhesively secure said applique sheets to said intensifying screens in an aligned condition.

14. Apparatus as recited in claim 13, wherein each of said applique, sheets is composed of a transparent material.

15. Apparatus as recited in claim 13, wherein said anti-stick protective sheet comprises a transparent material.

16. Apparatus as recited in claim 13, wherein said anti-stick protective sheet is selected from the group consisting of silicone coated paper and wax paper.

17. Apparatus as recited in claim 13, wherein said anti-stick protective sheet has a surface energy that is less than the surface tension of said adhesive surface.

18. Apparatus as recited in claim 13, wherein said adhesive surface of said first and second applique sheets comprise a pressure sensitive adhesive.

19. Apparatus as recited in claim 13, wherein said adhesive coating has a surface tension greater than the surface energy of said applique sheets.

20. Apparatus as recited in claim 13, wherein said applique sheets are selected from the group consisting of cellophane, polyvinyl chloride, polyester, polyethelene, polypropylene and cellulose acetate.

21. Apparatus as recited in claim 13, wherein said anti-stick protective sheet has a surface energy that is less than about 80%, preferably less than about 50%, more preferably ranges up to 25% of the surface tension of said adhesive surface.

22. Apparatus as recited in claim 18, wherein said pressure sensitive adhesive is selected from the group consisting of polyvinyl ethel ether, polyisobutylene and acrylate copolymer.

23. Apparatus as recited in claim 19, wherein said surface tension of said adhesive coating is greater than about 125%, preferably greater than about 200%, more preferably ranges above 400of said surface energy of said applique sheets.

* * * * *